United States Patent
Mann et al.

(10) Patent No.: US 12,344,580 B2
(45) Date of Patent: Jul. 1, 2025

(54) METHANE SEPARATION SYSTEM AND METHOD

(71) Applicant: Bennamann Services Ltd, Newquay (GB)

(72) Inventors: Christopher Mark Mann, St. Mawgan (GB); Edward Richard Yorke Gleadowe, Falmouth (GB)

(73) Assignee: BENNAMANN SERVICES LTD, Newquay (GB)

( * ) Notice: Subject to any disclaimer, the term of this patent is extended or adjusted under 35 U.S.C. 154(b) by 342 days.

(21) Appl. No.: 17/796,547

(22) PCT Filed: Jan. 29, 2021

(86) PCT No.: PCT/IB2021/050739
§ 371 (c)(1),
(2) Date: Jul. 29, 2022

(87) PCT Pub. No.: WO2021/152541
PCT Pub. Date: Aug. 5, 2021

(65) Prior Publication Data
US 2023/0048087 A1 Feb. 16, 2023

Related U.S. Application Data

(60) Provisional application No. 62/967,859, filed on Jan. 30, 2020.

(51) Int. Cl.
*C07C 7/14* (2006.01)
*B01D 53/00* (2006.01)
(Continued)

(52) U.S. Cl.
CPC .............. *C07C 7/14* (2013.01); *B01D 53/002* (2013.01); *C10L 3/104* (2013.01); *C12M 21/04* (2013.01);
(Continued)

(58) Field of Classification Search
CPC ........ B01D 2256/245; B01D 2257/504; B01D 2258/05; B01D 53/002; F25J 2205/20; F25J 2210/66; C07C 7/14
See application file for complete search history.

(56) References Cited

U.S. PATENT DOCUMENTS 3,864,927 A * 2/1975 Li ........................... F25J 1/0277
62/54.3
5,060,480 A * 10/1991 Saulnier ................. F25J 1/0221
62/913
(Continued)

FOREIGN PATENT DOCUMENTS

EP 2795177 B1 10/2014
FR 3050655 A1 11/2017
(Continued)

OTHER PUBLICATIONS

Description translation (Year: 1970).*
(Continued)

*Primary Examiner* — Filip Zec
(74) *Attorney, Agent, or Firm* — Rothwell, Figg, Ernst & Manbeck, P.C.

(57) ABSTRACT

Systems and methods for separating a biogas or other gaseous material into its constituent parts, including solid methane and carbon dioxide, using liquid nitrogen in a processing chamber. The individual parts may be extracted from the processing chamber. Separation and extraction can be performed on a mobile processing plant.

18 Claims, 9 Drawing Sheets

(51) Int. Cl.
*C10L 3/10* (2006.01)
*C12M 1/00* (2006.01)
*C12M 1/107* (2006.01)
*F25J 3/06* (2006.01)
*C02F 11/04* (2006.01)

(52) U.S. Cl.
CPC ............ *C12M 47/18* (2013.01); *F25J 3/0635* (2013.01); *F25J 3/0695* (2013.01); *C02F 11/04* (2013.01); *C10L 2200/0469* (2013.01); *C10L 2290/543* (2013.01); *F25J 2205/20* (2013.01); *F25J 2210/66* (2013.01); *F25J 2290/70* (2013.01)

(56) References Cited

U.S. PATENT DOCUMENTS

| | | | | |
|---|---|---|---|---|
| 6,006,545 | A * | 12/1999 | Tranier | F25J 1/0208 62/910 |
| 8,673,056 | B2 * | 3/2014 | De Bas | B01D 53/885 62/619 |
| 8,679,566 | B1 * | 3/2014 | Hancock | A23G 9/28 426/100 |
| 9,700,849 | B2 * | 7/2017 | Hironaka | B01D 63/00 |
| 11,204,196 | B2 * | 12/2021 | Ebert | F25J 1/0271 |
| 11,299,686 | B2 * | 4/2022 | Foody | B01D 53/62 |
| 12,152,816 | B1 * | 11/2024 | Royer | H01M 10/0569 |
| 12,163,736 | B2 * | 12/2024 | Han | F25J 1/0057 |
| 2006/0213370 | A1 | 9/2006 | Leonard et al. | |
| 2007/0292306 | A1 * | 12/2007 | Hirano | B01D 53/002 422/38 |
| 2015/0334774 | A1 * | 11/2015 | Schryver | G01K 3/10 219/442 |
| 2016/0261005 | A1 * | 9/2016 | Rustomji | H01M 10/0564 |
| 2021/0000104 | A1 * | 1/2021 | Kukal | A01N 1/162 |
| 2022/0339580 | A1 * | 10/2022 | Maddox | B01D 53/504 |

FOREIGN PATENT DOCUMENTS

| | | | | |
|---|---|---|---|---|
| GB | 1310707 A | * | 3/1973 | ............ F25J 1/0022 |
| WO | 2019030688 A1 | | 2/2019 | |
| WO | WO-2019122660 A1 | * | 6/2019 | ......... B01D 53/0462 |
| WO | 2020225794 A1 | | 11/2020 | |

OTHER PUBLICATIONS

Machine Translation of Description of WO (Year: 2019).*
International Search Report and Written Opinion issued in corresponding International Application No. PCT/IB2021/050739, dated May 27, 2021, 11 pages.

* cited by examiner

# METHANE SEPARATION SYSTEM AND METHOD

CROSS REFERENCE TO RELATED APPLICATION(S)

This application is a 35 U.S.C. § 371 National Stage of International Patent Application No. PCT/IB2021/050739, filed Jan. 29, 2021, designating the United States and claiming priority to U.S. Provisional Application No. 62/967,859, filed on Jan. 30, 2020, the disclosures of which are incorporated herein in their entirety by reference.

TECHNICAL FIELD

Disclosed are embodiments relating generally to processing of a gas or liquid, and in particular processing of biogas comprising methane to remove secondary materials such as carbon dioxide ($CO_2$).

BACKGROUND

Anaerobic digestion (AD) is a technique for converting organic matter into biogas, and ultimately, methane gas. Methane is often the primary component of natural gas, which provides an increasing percentage of centralized power generation. Anaerobic digestion can be used in attempts to reduce greenhouse gas emissions.

However, methane-based materials, such as biogas or liquefied biogas, contain certain unwanted components, including $CO_2$ or hydrogen sulphide. For instance, the biogas that results from anaerobic digestion of biomass, such as grass cuttings or other vegetative feedstock, typically consists primarily of methane (~60-70%), $CO_2$ (~30-40%) and a trace amount of hydrogen sulfide. Additionally, these individual components of a biogas may be separately useful. Certain techniques for cleansing or separation of such materials are provided in U.S. Pat. No. 9,927,067 to Mann et al., including filtering of hydrogen sulfide and use of one or more compressors coupled to a heat exchanger within a storage unit.

SUMMARY

According to embodiments, liquid nitrogen ($N_2$) is used to separate lighter methane from heavier $CO_2$. This can be accomplished by introducing a biogas to a chamber of liquid nitrogen, or vice-versa. The cold of the liquid nitrogen can cause the constituent parts of the biogas to separate from each other, for instance in solid form. Once separated, the constituent parts can be independently removed or stored. Additionally, the chamber itself may be sealed or otherwise covered for transport or additional processing. For instance, the cooling caused by the liquid nitrogen may be an initial phase of a liquefaction process for one or more components of the biogas, such as methane.

According to embodiments, a material processing system is provided that comprises a source, such as a storage tank, that contains a material for processing, such as a biogas. The system also comprises a processing chamber coupled to the source and containing a cold material, such as liquid nitrogen. In embodiments, the source material (e.g., the biogas) is comprised of at least a first part and a second part, and the system is configured such that the material is introduced to the liquid nitrogen in the processing chamber and the first part and the second part separate from each other. For instance, a methane part and a $CO_2$ part may separate from each other. This may be in solid form, and can include the first, methane part rising within the chamber while the second, $CO_2$ part descends within the chamber. In some embodiments, the source comprises an anaerobic digester configured to generate the material for processing.

According to some embodiments, a method of processing a material comprised of a mixture of at least a first part and a second part is provided. The method may begin with introducing the material to a reservoir of liquid nitrogen or other sufficiently cold medium to solidify the first part and solidify the second part. In certain aspects, the solidifying separates the first and second parts from each other. The method may also comprise extracting or storing one or more of the first and second parts. In some embodiments, the material is a biogas and the first part is methane and the second part is $CO_2$. In some embodiments, introducing the material comprises delivering biogas from a biogas source to a processing chamber containing the liquid nitrogen reservoir. Alternatively, the liquid nitrogen can be delivered to a chamber containing the material to be processed.

According to some embodiments, a method of generating a fuel is provided. The method may comprise, for instance, generating a biogas using an anaerobic digester, where the biogas is a mixture of at least a methane part and a $CO_2$ part. The method may further comprise combining the biogas with liquid nitrogen in a processing chamber, where the combining causes the methane part and the $CO_2$ part to each solidify and separate from each other. The processing chamber can then be sealed to store one or more of the methane part and the $CO_2$ part. In some embodiments, the methane and/or $CO_2$ parts can be extracted from the chamber. In this respect, the method may be for generating $CO_2$ in addition to, or instead of, the generating and extraction of methane. The extraction may be performed in conjunction with a phased warming process, for instance.

According to embodiments, materials can be extracted from a container. For example, a container may comprise multiple materials in solid form having different transition temperatures, such as solid methane and solid $CO_2$. In some embodiments, the contents of the container can be warmed in a first and second phase, where the first phase warms the materials sufficiently such that the solid methane becomes liquid. In the second phase, with additional warming, the solid $CO_2$ become liquid or gas. In each phase, the respective liquid or gaseous materials can be extracted from the container. In some embodiments, residual liquid nitrogen may be boiled off in another, third phase, for instance, before the phases for the $CO_2$ and methane.

According to some embodiments, a method of processing a material comprised of a mixture of at least a first part and a second part is provided. The method may comprise the steps of introducing the material to a reservoir of liquid nitrogen (e.g., in a processing chamber) to solidify the first part and solidify the second part, wherein the solidifying separates the first and second parts from each other; and extracting or storing one or more of the first and second parts. In some embodiments, the material is a biogas and the first part is methane and the second part is $CO_2$. In some embodiments, introducing the material comprises delivering biogas form a biogas source to a processing chamber containing the liquid nitrogen reservoir. In some embodiments, the method comprises circulating liquid nitrogen through the processing chamber to maintain a desired temperature in the processing chamber or of the liquid nitrogen reservoir. In some embodiments the method comprises cooling a liquid nitrogen source using vented nitrogen from the processing chamber or reservoir, and/or liquefying the vented nitrogen and providing the liquefied nitrogen to the processing chamber or reservoir. In some embodiments, the vented nitrogen may be used for cooling input biogas, for instance, at an input pipe or hose.

According to embodiments, a method is provided for mobile processing of materials, comprising the steps of: transporting a cooling material to a source site; obtaining a gaseous material at the source site, where the gaseous material comprises of a mixture of at least a first part and a second part; and combining the gaseous material with the cooling material in a processing chamber to solidify at least one of the first part and the second part, where the solidifying separates the first and second parts from each other. In some embodiments, both the first and second parts are solidified. In some embodiments, the cooling material is liquid nitrogen, the gaseous material is biogas, the first part is methane, and the second part is $CO_2$. The method may also comprise extracting or storing one or more of the first and second parts in solid, liquid, or gaseous form. This may be in conjunction, for instance, with a phased warming of at least one of the first and second parts in the processing chamber. The phased warming may comprise warming at least the first part (e.g., methane) to a first target temperature in a first warming phase, and extracting the first part from the processing chamber in liquid or gaseous form. It may also comprise warming at least the second part (e.g., $CO_2$) to a second target temperature in a second warming phase and extracting the second part from the processing chamber in liquid or gaseous form. According to embodiments, the source of the gaseous material may be a remote anaerobic digester or covered gas source. In some embodiments, at least one of the separating, phased warming, and the extracting is performed while the mobile plant is in transit away from the source site.

According to embodiments, a mobile processing plant comprises a vehicle and a separation system according to any of the foregoing, where the separation system is mounted on the vehicle. In some embodiments, the vehicle is a car, truck, tractor, boat, or aircraft. In certain aspects, processing biogas at an anaerobic digester site (or while leaving a site) can include separating and converting the constituent parts in solid phases according to any of the foregoing, and transporting one or more of the constituent parts off site.

BRIEF DESCRIPTION OF THE DRAWINGS

The accompanying drawings, which are incorporated herein and form part of the specification, illustrate various embodiments.

Together with the description, the drawings further serve to explain the principles of the disclosure and to enable a person skilled in the pertinent art to make and use the embodiments disclosed herein. In the drawings, like reference numbers indicate identical or similar functionally.

DETAILED DESCRIPTION

Figure 1:
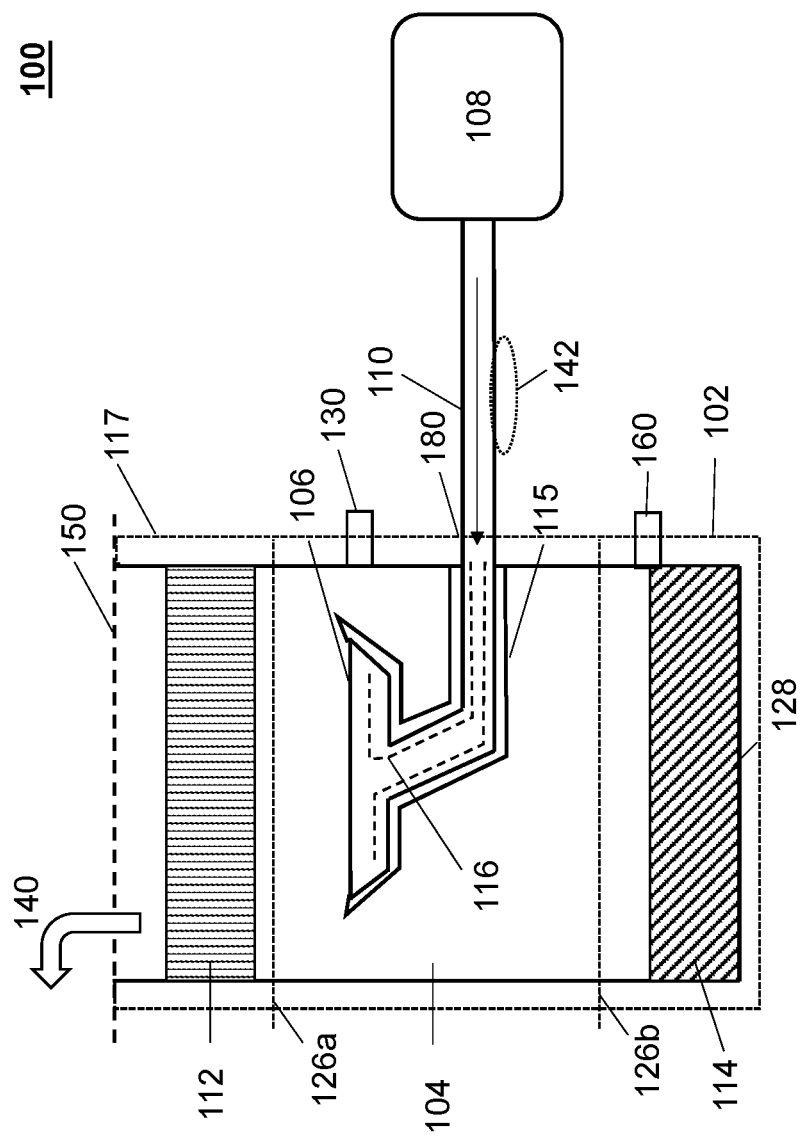
FIG. 1 illustrates a processing system according so some embodiments.

There remains a need for processing techniques for materials with varied constituent parts, such as methane-based materials, in which individual constituent parts can be separated or otherwise removed in an efficient and cost effective manner. Such techniques can enable local or mobile processing and extraction of such materials, for instance, using a vehicle.

According to aspects of the disclosure, bio-methane can be readily generated from biomass waste using anaerobic digestion, and biomass is abundant globally, thus offering a vast potential energy source derived from sunlight. However most biomass is created in remote areas where there is little access to power or gas transmission networks making it difficult to exploit. This issue may also be applicable to other sources of gaseous materials, such as natural gas sourced at off-shore sites (e.g., ocean rigs or underwater wells) or other difficult land-based geographic locations (e.g., fracking sites or ground wells). Development with respect to mobile processing plants may address certain problems, for instance, by processing the raw biogas at the anaerobic digester site, or while in transit, by separating and converting the constituent parts (e.g., methane and $CO_2$) into their liquid or solid phases so that they can be transported to other locations by road or boat. Embodiments may be applied in connection with such mobile processing.

Existing cryogenic processing offers many advantages, but often requires significant amounts of power to drive the refrigeration and compression systems that may be needed by existing systems. To address power needs, power can be generated (e.g., on site) by using some of the generated biogas. However, refrigeration and compression systems are often complex and expensive, and mounting them onto a moving platform presents many practical issues in addition to the introduction of new expenses. According to embodiments, a process is provided that alleviates certain disadvantages of existing systems by taking the necessary "cold" required for processing onsite, for instance, in the form of liquid nitrogen. In certain aspects, this means that complex refrigeration systems can be located at a distance from the biomass source, for instance, at a location where there is either sufficient power or an abundance of renewable energy such as wind, hydro, or solar for example.

According to embodiments, a biogas processing plant comprises a cryogenic reservoir of liquid nitrogen sized to provide sufficient "cold" to drive a separation process, and is further configured to extract or otherwise take away the resultant solid or liquid methane and/or solid or liquid $CO_2$. This can reduce the cost and complexity of a mobile processing plant significantly. It may also increase overall yield by removing the need to use some of a biogas (e.g., the methane of the biogas) to power the process. Because nitrogen is an inert gas, aspects of the disclosure reduce the cost of the refrigeration equipment as there is no need to make it compliant with explosive atmospheres required for methane processing. In addition, the increased yield of the biogas $CO_2$ and liquid or solid methane products, coupled with the growing availability of cheap renewable energy at the liquid nitrogen generation site, are benefits. This is particularly true for intermittent renewables, as liquid nitrogen production can be increased at times of high energy availability with adequate liquid nitrogen storage being achieved by oversizing the storage vessel onsite. Moreover, overall energy efficiency can be improved through the use of heat exchangers that use the cold nitrogen boil-off gas to pre-cool the biogas. For example, a feed pipe delivering biogas to the processing chamber may be cooled in one or more locations using cold boil-off nitrogen from the processing chamber. If renewable energy is available at the biogas generation site, then this can be used to further assist the processes. For instance, the system may be coupled to a wind generation source, which can power one or more elements of the system (e.g., a cooling process).

According to embodiments, a reservoir of liquid nitrogen ($N_2$) is used to separate lighter solid methane from heavier solid carbon dioxide ($CO_2$). For instance, the liquid nitrogen reservoir may be at ~77 degK (assuming 1 bar pressure). Because methane freezes (solidifies) at ~90 degK, and solid $CO_2$ forms at 194 degK, introduction of a non-homogeneous material (e.g., a biogas) comprising methane and $CO_2$ to the liquid nitrogen reservoir results in separation of the constituent parts. This may be with both the methane and $CO_2$ separating in solid form. Moreover, because of the relative densities, the solid methane will move to the surface of the reservoir, while the $CO_2$ will sink. In some embodiments, the methane may separate in liquid form. The relative transition temperatures can enable easy extraction and or storage, for instance, using physical removal of solids, phased warming for extraction of liquids, and/or sealed or actively refrigerated storage after separation.

Referring now to FIG. 1, a system 100 for processing a multi-component material, such as biogas containing methane and $CO_2$, is provided according to some embodiments. While this example uses methane-based biogas, other materials may be used according to embodiments. For instance, other gases or liquids, such as natural gas from ground and sea sources, can be processed using the disclosed systems and methods. In this example, the methane-based material (e.g., biogas in this example) is delivered to a processing chamber 102. While illustrated as a single chamber, the chamber may have separate sub-chambers in embodiments. The chamber 102 is filled, including partially filled, with a "cold" material 104, such as liquid nitrogen. The material to be processed may come from source 108, and flow along a pipe or hose 110 to opening 106, which introduces the material to the liquid nitrogen 104. The pipe 110 may interface with the processing chamber 102 at an input 180, which in some embodiments, may comprise one or more valves. While illustrated in FIG. 1 with a direct connection via pipe 110, embodiments may use a processing chamber 102 that is not directly coupled to source 108. Also, while a pipe is described, a hose or other conveyance mechanism may be used. Additionally, in some embodiments, biogas generation and the separation in chamber 102 may occur at different locations. For example, biogas from a source 108 at a first location may be transported to chamber 102 at a second location. Additionally, processing in chamber 102 may occur away from the location of source 108. This may be, for example, where processing chamber 102 is mounted on a vehicle, such as a truck or ship. In certain aspects, chamber 102 may be operated in transit.

To prevent the formation of solid $CO_2$ or methane in the pipe 110 leading to the opening 106, the pipe 110 may be insulated using an external vacuum. This can be provided, for instance, through the use of an outer pipe 115 sealed from the vessel containing the liquid nitrogen. The biogas opening can be optimised to provide the optimum bubble size to allow the necessary separation conditions. For instance, it may be tapered as illustrated in FIG. 1. The flow can be adjusted by increasing or reducing the pressure of the biogas. This could include, for instance, the use of one or more valves, compressors, or regulators between the biogas source and processing chamber. Such feedback and control could be implemented with a sensing and processing system, such as device 800 described in connection with FIG. 8. In some embodiments, a heater 116 can be incorporated within the vacuum space and around the opening to ensure that blockages to the feed pipe or openings are avoided or cleared. In some embodiments, a solid insulator is applied around the pipe 110. In some embodiments, feed pipe 110 delivering biogas to the processing chamber 102 may be cooled in one or more locations using cold boil-off nitrogen 140 from the processing chamber 102, for instance in one more locations/elements 142. This could be, for instance, a heat exchanger or other element that places boil-off case sufficiently close to input gases to result in cooling. In some embodiments, the cooling 142 of the input gas along pipe 110 can be used to freeze out water from the gas, increasing its purity. While nitrogen is used as an example here and elsewhere, other inert liquid gases, such as argon, could be used instead of nitrogen in some embodiments as the cooling material.

Because of the differing freezing temperatures of the component parts of the source material and liquid nitrogen (or other cooling material, such as liquid argon), the parts may separate into a first part 112 and a second part 114. According to embodiments, the first part 112 and second part 114 separate in solid form. For instance, a biogas introduced to liquid nitrogen 104 may separate into solid methane 112 and solid $CO_2$ 114. Further, and according to some embodiments, due to differing densities, the first part 112 (e.g., solid methane) may move to the surface of chamber 102 while the second part 114 (e.g., solid $CO_2$) may sink to the bottom of the chamber. Liquid nitrogen may boil off 140 during the process. In some embodiments, the amount of liquid nitrogen 104 is sized to match the amount of input materials such that the processing in chamber 102 is a batch process. If additional liquid nitrogen 104 remains after processing of the source material is complete, it may be allowed to boil off, leaving only the constituent parts in the chamber 102.

Under certain conditions, methane may be miscible in liquid nitrogen providing a lighter solution that allows the solid $CO_2$ to drop to the bottom, but allow the methane/nitrogen solution to be removed to a separate chamber as a liquid, and the nitrogen allowed to boil off due to its lower boiling temperature. This could leave, for instance, solid $CO_2$ in chamber 102 with the methane and/or remaining liquid nitrogen moved to a different container.

The source 108 may be a storage tank and/or anaerobic digester, such as described in U.S. Pat. No. 9,927,067 (WO2013/093601) to Mann et al., which is titled "Liquid Methane Storage System Method," filed Dec. 20, 2012, and incorporated by reference herein. The biogas generation and methane storage/cooling techniques described therein may also be used with the embodiments of the present disclosure. For instance, chamber 102 may be a tank (e.g., when closed) as described in U.S. Pat. No. 9,927,067, and utilize one or more of the cooling and pressure control mechanisms described therein. According to embodiments, processing chambers and/or storage tanks described herein can use vented methane to generate power (e.g., with an engine or fuel cell), and then use that power to run a cooling cycle for the chamber or tank, wherein the cooling cycle reduces temperature and/or pressure. One or more of a refrigerator device or compressor coupled to a heat exchanger may be used in some embodiments for cooling. In certain aspects, the Joule Thompson effect may be utilized to cool gas, for instance, when passed through a small orifice. One or more of the pressure and temperature controls, including venting and operation of valves, can be remotely controlled and monitored. In some embodiments, a tank with such cooling and pressure control mechanisms may be used to store methane (or $CO_2$) following extraction from chamber 102 according to embodiments.

According to embodiments, the material (e.g., biogas) flowing along pipe 110 may be pressurized. This pressurization may eliminate the need for a valve between the source 108 and chamber 102, and can prevent unwanted flow of liquid nitrogen 104 towards source 108. However, in some embodiments, a valve may be used between pipe 110 and chamber 102.

According to some embodiments, the system 100 may be used for batch processing, in which the reservoir of liquid nitrogen 104 is used completely to process a specific amount of biogas from source 108. In some embodiments, additional liquid nitrogen may be added to system 100 for continued processing of biogas, for instance through an inlet 130. Alternatively, in some instances, processing of the biogas may finish with some liquid nitrogen 104 remaining in chamber 102. It may be convenient to re-liquefy the nitrogen gas boil-off using a refrigeration system at the cost of additional power.

While illustrated in FIG. 1 as an open-topped chamber, the chamber 102 may be a closed tank (e.g., a cryogenic tank under vacuum during processing). Additionally, a top 150 may be added to chamber 102 to form a closed tank. In some embodiments, after processing, the solid methane and/or $CO_2$ are sealed in chamber 102 (e.g., under vacuum) for storage and/or transportation. The solid methane may remain solid, or turn to liquid form within the tank 102 over time. Sealing the chamber/tank 102 may comprise closing one or more valves or openings, such as a valve or opening connected to a source 108 of biogas or an inlet for liquid nitrogen 130, and/or adding the top member 150.

Once separated and moved to respective tanks as needed, both solid $CO_2$ and methane may be allowed to melt back to liquid for more convenient handling and/or extraction. In this case, the vessel used (e.g., chamber 102) may be designed to be pressurised such that the ideal liquid conditions and temperature can be set according to is further use and sale. For example, $CO_2$ liquid can be stored non-cryogenically in a vessel that can support the necessary pressure. Liquid methane typically must be stored cryogenically, but the pressure at which it is stored can be set according to its temperature. For instance, one or more of the cooling and pressure control systems could be included, as discussed above. Refrigeration features could also include, for instance a Brayton cooling system, cascade system, or another cooling element. The temperature may also be used to control pressure. This can be useful, for example, if methane needs to be ejected at high flows for large engine fuelling, negating the requirement for a compressor.

According to embodiments, one or more of the solid methane and/or $CO_2$ may be extracted from the chamber 102 in solid form. In some embodiments, the $CO_2$ is at least 99% pure, and in some instances, 99.99% pure.

In some embodiments, the chamber 102 may have one or more dividers 126a, 126b, which can serve as platforms to support solidified materials, for instance, to prevent movement of solidified materials. For example, solidified methane may accumulate above divider 126a. According to some embodiments, the dividers are porous or semi-permeable. Alternatively, they may be solid. In some embodiments, the dividers 126a, 126b, may be inserted to create sub-chambers within chamber 102. While illustrated as horizontal dividers, the dividers 126a, 126b may be arranged vertically or off-axis. Additionally, one or more of dividers 126a, 126b can be sealed to maintain vacuum or prevent material flow during extraction from another sub-chamber. For instance, 126b may be sealed when solidified $CO_2$ 114 is extracted from the bottom of tank 102. In certain aspects, the bottom surface 128 of tank 102 may be hinged or otherwise removable to allow extraction of the solidified $CO_2$ 114 from the bottom of chamber 102.

According to embodiments, hydrogen sulphide may be removed from the source material (e.g., biogas), for instance via a filter, before reaching the chamber 102.

Though not illustrated, the chamber 102 may include a cooling circuit for reducing the temperature of the liquid nitrogen. According to embodiments, the cooling circuit may utilize boil-off gaseous nitrogen 140 as a source of cold. In some embodiments, a refrigeration element is used to cool the material in chamber 102. This could include, for instance a Brayton cooling system, cascade system, or another cooling element. In some embodiments, a heating element may be included within or on a surface of the chamber, such as a resistive heating element.

In some embodiments, the system 100 may be adapted for warming of its contents. For instance, one or more of the process chamber 102, the solid methane 112, or solid $CO_2$ 114 may be warmed. This can result in one or more of the solid constituent materials transitioning to a liquid form. This may be useful, for instance, for extraction. In some embodiments, liquid may be extracted via an outlet 160, which may comprise one or more valves. Such warming may also include transition to the gas phase. In a gas phase, one or more of the materials (e.g., the $CO_2$) could then be vented from the chamber 102. In some embodiments, the warming is a phased warming, in which warming is performed with different phases or steps. For instance, the temperature may be increased to a first temperature during a first phase such that a first material transitions to liquid form. This could be, for instance, solid methane transitioning to liquid methane at 90 degK or more. The methane could then be removed from the tank in liquid form while the carbon dioxide stays in solid form. In a second phase, the temperature may be increased to a second level, such that a second material (e.g., $CO_2$) transitions to liquid or gas for removal. The temperature for $CO_2$ transition may be at least 194 degK. These are examples, and more or less warming/holding phases may be used according to embodiments and depending on material. In some embodiments, the temperature is held at least long enough during a given phase to allow the target material to fully transition to the desired form and be removed. In some embodiments, only a single material transition is targeted in the phased warming process. For instance, a first phase may raise the temperature to a sufficient temperature to get liquid methane, while the second phase maintains a desired temperature without causing the $CO_2$ to turn to liquid. For instance, the second phase may hold the tank and its contents between 90 and 194 degK. This may require activation of one or more refrigeration elements. According to embodiments, the transition temperatures may vary depending on the pressure of the tank or processing chamber.

According to embodiments, the warming (e.g., the phased warming) is accomplished by allowing the materials to naturally warm. This could be, for example, over time and/or by deactivating one or more refrigeration elements. In some embodiments, a heater may be activated to help control the warming. The heater may be mounted, for instance, within the chamber 102 or on one of its walls. In some embodiments, the temperature of the system may be controlled by device 800, for instance, through feedback from one or more temperature and/or pressure sensors. One or more refrigeration units may be reactivated as needed to control the temperature, or for storage in a particular phase after the phased warming and extraction is complete.

Figure 2:
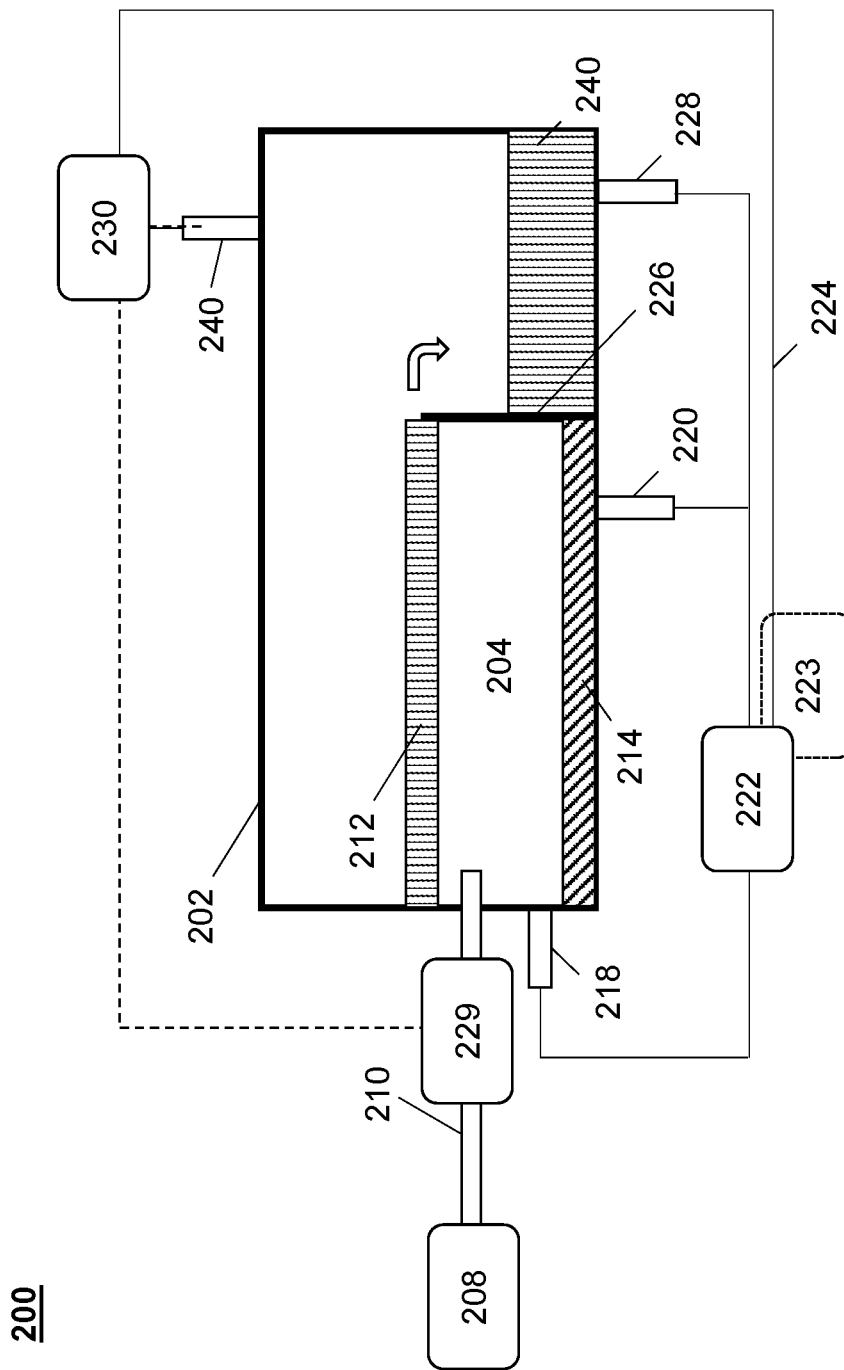
FIG. 2 illustrates a processing system according so some embodiments.

Referring now to FIG. 2, a material processing system 200 is provided according to some embodiments. The system may comprise a chamber or tank 202 for separating biogas received from a source 208 using liquid nitrogen 204, provided via pipe 210. The biogas may be separated into its constituent components methane 212 and $CO_2$ 214 upon introduction to the liquid nitrogen 204. In some embodiments the methane 212 is separated in solid or liquid form upon cooling from liquid nitrogen 204, while the $CO_2$ is separated in solid form 214. As with system 100, the system 200 can similarly be implemented using different source materials and cooling materials according to embodiments.

In some embodiments, the liquid nitrogen 204 is provided to the tank 202 via inlet 218 from liquid nitrogen source 222. In certain aspects, liquid nitrogen 204 is flowed from the inlet 218 to an outlet 220 or 228, and returned to source 222, which can include a cooling circuit 223. The source 222 and cooling circuit 223 may comprise a single unit. In some embodiments, gaseous nitrogen 240 is provided via a switched valve 230 to source/cooling circuit 222, 223 as a source of cold in a feedback loop, which can re-liquefy the nitrogen gas to replenish the level of the liquid nitrogen reservoir and also make the system closed loop. This would also have the advantage of ensuring that the purity of the nitrogen can be maintained. In some embodiments, the system can be operated indefinitely provided that there is sufficient power available to power the cooling circuit 223, and a sufficient supply of source materials. In some embodiments, additives (e.g., dust, nanoparticles, or other fillers that could help the separation as nucleation centers) are injected, which can enhance the solidification of the constituent parts 212, 214. The may be injected directly into the chamber 202, or delivered with one or more of the materials (e.g., biogas or liquid nitrogen). In certain aspects, the cold boil-off nitrogen gas 240 can be sent via a heat exchanger 229 positioned on the biogas input to increase the overall efficiency of system 200 by recovering the cold originally expended in the production of the liquid nitrogen. In some embodiments, the flow of liquid nitrogen 204 to the tank 202 is controlled to match the amount of biogas provided to the tank 202. Such control may be provided by a sensing and control device, such as device 800 having one or more sensors.

According to embodiments, the measurement of nitrogen boil-off gas flow and vessel temperature and pressure, combined with knowledge of the original makeup of the biogas constituents can be used to calculate the rate of solid formation and separation. The volume of the individual compartments also provide knowledge of the process rate. The combination of the above parameters can then be used to adjust the process conditions such as liquid nitrogen re-entry flow rate and usage. According to embodiments, the purity sensor and/or flow sensor is sensor configured to (i) generate one or more sound waves passing through a fuel (e.g., liquid or gas), and (ii) measure a velocity of one or more sound waves passing through the fuel. The velocity can indicate one or more of flow rate and/or purity. Such sensors as described in WO 2019/229496A1, titled "Method and System of Determining a Quality of a Fuel," filed May 29, 2018, and incorporated herein by reference.

According to embodiments, liquid or solid methane may flow over a barrier 226 and collect in a region 240 of tank 202. The barrier 226 may contain the liquid nitrogen 204, as well as the solid $CO_2$ 214, while allowing liquid or solid methane to flow to region 240. In this respect, barrier 226 may separate the tank 202 into first and second regions for $CO_2$ and methane collection, respectively. Barrier 226 may be arranged vertically (e.g., as a wall), within the processing chamber. In some embodiments, the solid methane may be extracted in solid form from tank 202. In some embodiments, the methane may be decanted in liquid form. In some embodiments, the methane is extracted in liquid form via an outlet, such as outlet 228 (or other outlet) as part of a phased warming processes.

In some embodiments, tank 202 may be sealed and the methane 212 stored therein. This could include, for instance, closing one or more of inlets/outlets 218, 220, 228, 2240, and an interface to source 208. Boil-off methane (and any remaining nitrogen) may be vented through an outlet, such as outlet 240. In order to control the process and storage, each of the inlets/outlets may comprise a valve, and the valves may be remotely controllable (e.g., via device 800). As with system 100, system 200 may also use phased warming for extraction or storage of constituent parts, for instance, in liquid form.

According to embodiments, the tank of FIG. 1 or FIG. 2 is insulated to the highest degree possible to prevent unnecessary heat ingress. This can be achieved, for instance, through the use of an outer skin on chamber 102 capable of supporting a vacuum 117. Traditionally, vacuum vessels require a circular cross section due to the atmospheric pressure pushing in on the outer skin. However, as described in WO 2019/102357A1, titled "Liquid Methane Storage and Delivery System," filed Nov. 20, 2018, which is incorporated by reference, complex shapes and sizes can be realized. This removes the need for circular cross section vessel which can increase the batch production volumes possible on a mobile platform and also allows different tank structure to be realised that may add in the solid separation process. It also allows the internal tank construction to allow high pressure if required, which in turn can allow a greater degree of the process variables. For example, the $CO_2$ tanks can be constructed with different volumes and pressure ratings according to the end product requirement. For example, the tanks and processing chambers used in the present disclosure can have a non-cylindrical shape, including rectangular, round-rectangular, or irregular. This may help mounting of a tank or processing chamber on a vehicle, which may have spatial and shape constraints.

According to embodiments, one or more of the systems and methods disclosed herein may be implemented as part of a mobile processing plant, for instance, as discussed in connection with FIG. 6 and system 600. For instance, one or more of the methane and/or $CO_2$ inputs and/or outputs, as well as any cold box, of a mobile processing plant can be implemented using devices and systems shown in FIGS. 1 and 2. Additionally, any methane liquefaction process may be performed using inputs and processes that begin with the systems and processes described with respect to FIGS. 1 and 2. The same applies to $CO_2$ removal processes and systems.

Figure 3:
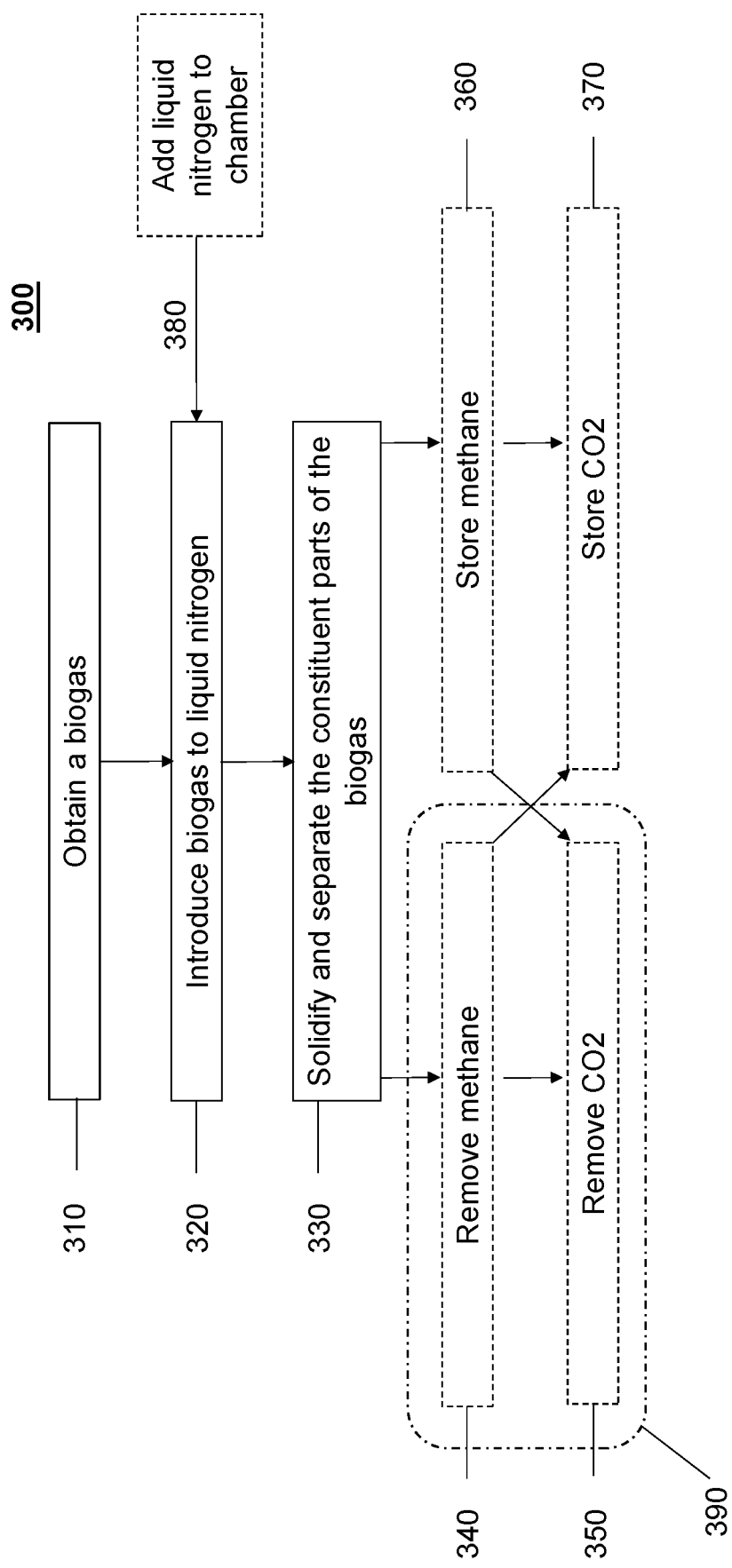
FIG. 3 is a flow chart showing methods according to some embodiments.

Referring now to FIG. 3, a process 300 is provided for processing a material, such as a biogas, according to embodiments. The method may be performed, for instance, using system 100 or 200. In some embodiments, the process may be performed on a mobile processing plant 610.

The process 300 may begin, for example, with step 310 in which a material (e.g., biogas) is obtained. This could include, for instance, using a biogas storage, such as a tank, and may further include generating biogas according to an anaerobic digestion process. This could include, for instance anaerobic digestion of green vegetative feedstock, as well as the digesters and sources shown in FIGS. 9A and 9B. While biogas is used as the example in process 300, other types of gas and gas sources may be used with the process. For instance, the source for step 310 may be a natural gas source, such as an offshore source or ground well. Similarly, a storage tank for such natural gas materials may be used as the source for obtaining in step 310. In some embodiments, the process 300 may include sealing a gas source to capture the material to be processed. This may be, for instance, using one or more membranes and/or covers as described with respect to FIGS. 9A and 9B.

In step 320, the biogas is introduced to liquid nitrogen. This could include, for instance, venting the biogas into a liquid nitrogen reservoir. In some embodiments, the biogas is introduced at an increased pressure. Alternatively, step 320 may comprise introducing liquid nitrogen to a store of biogas. Thus, and according to embodiments, step 320 may comprise different forms of combining a biogas (or other gas or liquid having constituent parts) and a cooling material, such as liquid nitrogen.

In step 330, at least one of the constituent parts of the material (e.g., methane and carbon dioxide for most biogas) solidifies due to the low temperature of the liquid nitrogen. For instance, at least two constituent parts solidify in some embodiments. While liquid nitrogen is used as an example in process 300, other cooing materials may be used, such as liquid argon. Given the differing densities, the materials also separate from each other. For example, the methane may rise to the top of the reservoir while the carbon dioxide sinks to the bottom of the chamber. The solid materials may then be removed (steps 340 and 350) or stored (steps 360 and 370). According to embodiments, and as illustrated in FIG. 3, the methane may be removed (340) and the carbon dioxide stored (370), or the carbon dioxide removed (350) and methane stored (360). That is, the steps 340, 350, 360, and 370 may be optional and interchangeable.

According to embodiments, one or more the storage and removal steps 340, 350, 360, and 370 may be performed for the materials in solid form. That is, methane and/or $CO_2$ can be removed and stored in solid form. In some embodiments, removal may be in liquid form. For instance, one or more of the constituent materials may be warmed and removed in liquid form for steps 340 and/or 350. This may be part of a phased warming process 390.

In some embodiments, the solid or liquid methane is stored in a specific sub-region of the processing chamber, such that it is separate from one or more of the liquid nitrogen and $CO_2$, and may be further separated from these locations for processing of biogas.

In some embodiments, the process 300 is a batch process that runs until all liquid nitrogen is used. The generated methane (or $CO_2$) may then be stored or extracted. In some embodiments, more liquid nitrogen is added at step 380. Thus, one or more subsequent steps may be repeated. For instance, additional biogas may be processed. This may be based, for instance, on one or more measurements from a sensor. This process may be controlled, for instance, using device 800 and one or more sensors. According to some embodiments, adding liquid nitrogen 380 comprises circulating liquid nitrogen through a processing chamber, for instance, as illustrated in FIG. 2. Vented gases may be used to help cool the process, as described in connection with systems 100 and 200.

Figure 4:
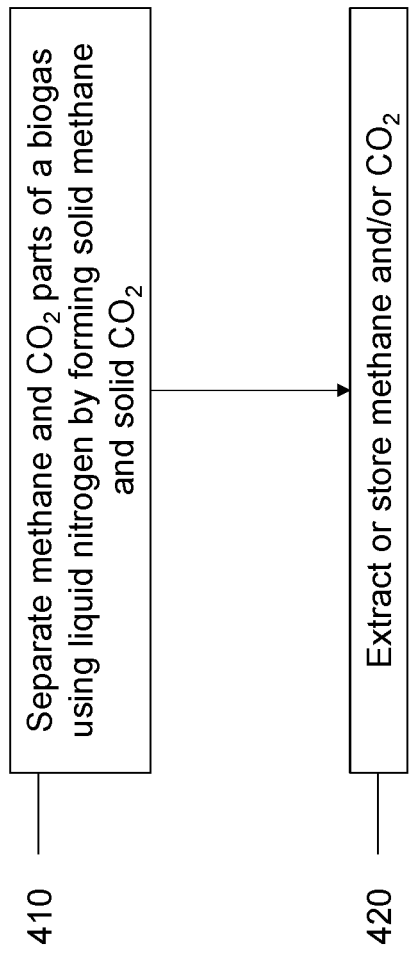
FIG. 4 is a flow chart showing methods according to some embodiments.

Referring now to FIG. 4, a process 400 is provided for processing a material, such as a biogas, according to embodiments. The method may be performed, for instance, using system 100 or 200 as described above. The process 400 may being with step 410, which comprises separating methane and $CO_2$ parts of a biogas using liquid nitrogen by forming solid methane and solid $CO_2$. In step 420, the constituent materials may be extracted or stored. Although described with solid-form constituent parts, the process may be implemented by separating one or more of the materials in their liquid form according to embodiments. In some embodiments, at least one of steps 410 and 420 is performed in a mobile processing plant. For instance one or more of steps 410 and 420 may be performed in transit from a biogas source.

Figure 5:
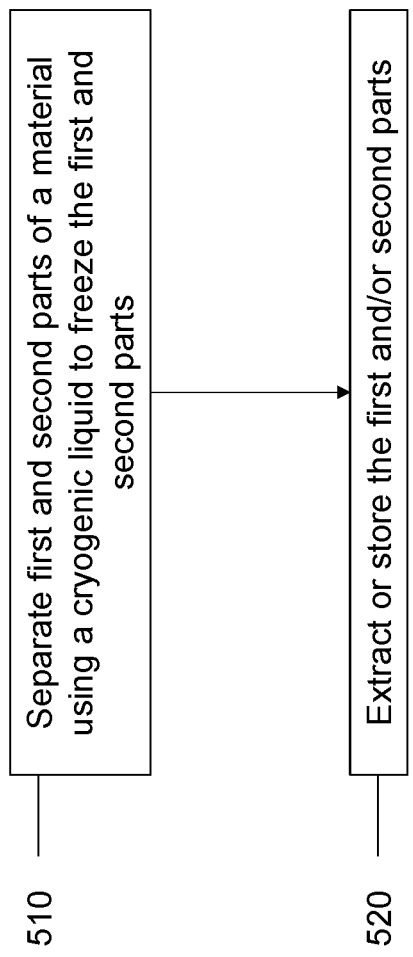
FIG. 5 is a flow chart showing methods according to some embodiments.

Although methane is used as an example, the storage, cleansing, and separation techniques and systems described herein can be used for other gaseous or liquid materials that have component materials having differing freezing/solidification temperatures than each other or substantially different densities. Referring now to FIG. 5, a generalized process is provide for separating 510 and extracting and/or storing 520. In step 510, first and second parts of a material are separated using cryogenic liquid (e.g., a reservoir) to freeze at least one of the first and second parts. In step 520, the one or more of the resultant parts are extracted (e.g., from a processing chamber) and/or stored. In some embodiments, the material used for step 510 is any cooling material having a suitable temperature to selectively separate the relevant parts of the material under process. As with other embodiments, the extraction and/or storage of step 520 may be in liquid or solid form.

Figure 6:
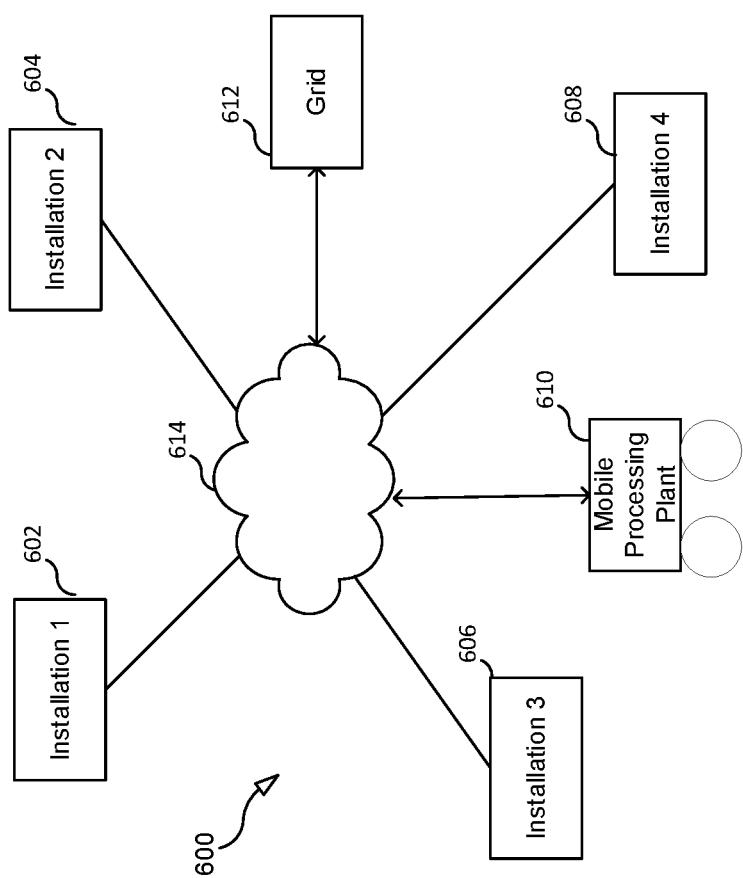
FIG. 6 illustrates a system according to some embodiments.

Referring now to FIG. 6, FIG. 6 illustrates an exemplary system 600 according to some embodiments.

As shown, source sites 602-608 may be communicatively coupled with a logistics coordination center 614. Logistics coordination center may also be communicatively coupled to one or more mobile biogas processing plants 610 and one or more grids 612. Each of source sites 602-608 may have one or more anaerobic digesters (ADs) associated with it. This could include, for instance, anaerobic digesters for green vegetative feeds stock, as well as gas collection membranes as described with respect to FIGS. 9A and 9B. The source sites may include, for instance, farms. In some embodiments, the sites are dairy cow farms, where the AD installations include covered slurry lagoons where cow manure or other farm-related biomass is fed into the anaerobic digesters shown in FIGS. 9A and 9B, and/or grasslands where grass clippings and related biomass is fed into the anaerobic digesters of FIGS. 9A and 9B. Other forms of AD can be used, including one more tanks. In some embodiments, the tanks may be relatively small, and the total number of tanks may be set according to a customers intended use and/or the amount of land that will be used to supply feedstock. In certain aspects, a PH gradient and temperature gradient can be maintained across the tanks. An AD may include an inlet for receiving feedstock and a macerator to mulch, agitate and/or separate components of the feedstock during anaerobic digestion. In some embodiments, the gas output from each tank is controlled via a latching gas valve. In certain aspects, the valve may be remotely controllable, for instance, via local or remote computer such as device 800. In some embodiments, the feedstock needs to pass through several different stages of digestion. For instance, it may pass from an initial aerobic hydrolysis/bacterial phase which breaks down insoluble polymers, such as carbohydrates, and makes them available for other bacteria. This phase also provides significant levels of heat which can be used to establish a rapid thermophilic phase, followed by a slower mesophilic phase used to digest the remaining material and produce the final digestate.

According to embodiments, each source site 602-608 may also include one or more sensors (e.g. measuring biogas level, concentration, power, etc.). One or more mobile biogas processing plants 610 may serve the installations, and the logistics coordination center 614 may monitor the one or more sensors form the different installations and coordinate movement and processing of the mobile biogas processing plants 610 based at least in part on the sensor readings. Mobile processing plants 610 may each include, for example, biogas separation and a methane liquefiers. For instance, the mobile processing plants 610 may include systems described with respect to FIGS. 1 and 2, and may be configured to performed processes as described with respect to FIGS. 3, 4, 5, and 7.

Logistics coordination center 614 may also communicate with grid 612, and may coordinate delivery of the mobile biogas processing plants 610 to supply power to grid 612 based on such communication. Logistics coordination center 614 may also receive information about current pricing of biogas, or power provided by the biogas, as well as information regarding contracts or other interest in parties receiving biogas. Logistics coordination center 614 may also receive readings from the mobile biogas processing plants, including their current location, capacity for carrying additional biogas, and additional scheduling related information e.g. indicating their availability for processing operations. Some or all of this information that logistics coordination center 614 receives may be used in making resource allocation decisions.

While a single logistics coordination center 614 is illustrated, it is noted that the logic for the center 614 may be housed together or may be spread out geographically in many different processing nodes. Additionally, there may be multiple logistics coordination centers 614. These multiple centers 614 may be responsible for disjoint sets of source sites, overlapping sets of source sites, or the same sets of source sites. For instance, the multiple centers 614 may communicate with each other regarding their respective capacities and capabilities, and coordinate sharing of resources associated with the respective centers 614. For instance, an association of local farmers, or a political entity, may be responsible for coordinating resources in a given area. That association or political entity, however, may also have agreements with other neighboring associations and political entities regarding sharing of resources. In such a circumstance, it may be that an available mobile biogas processing plant 610 from one association or political entity is sent to service an installation associated with another association or political entity based on need and availability.

Resource allocation decisions made by logistics coordination center 614 may have one or more different strategic goals. For instance, minimization of distance travelled by the mobile processing plants 610 may be one goal; maximizing price received for the biogas may be another goal; and ensuring that each anaerobic digester does not reach a critical capacity level may be another goal. Other goals are also possible, such as ensuring that total time where a certain digester capacity level is exceeded is minimized. Logistics coordination center 614 may attempt to balance one or more of these goals, and may assign priorities to them. Algorithms including machine-learning algorithms may be employed by logistics coordination center 614 to manage resources while ensuring compliance with the different goals.

While embodiments describe coordination and selection between source sites, a single site may be monitored and independently selected for processing, for instance based on one or more measurement of its biogas.

According to embodiments, one or more of the mobile processing plants 610 is a vehicle. For instance, a vehicle 610 may comprise one or more systems described with respect to FIGS. 1 and 2, and configured to perform processes as described with respect to FIGS. 3, 4, 5, and 7. Examples of vehicles include cars, trucks, and tractors. Other examples may include sea-based or air-based vehicles, such as boats (e.g., tankers) and aircraft. For instance, the system 600 may be implemented with ground-based vehicles and source sites 602-608, but in some embodiments, can be implemented with sea-based vehicles and source sites 602-608. For instance, one or more the source sites 602-608 may be an offshore or other sea-based well or extraction site, with vehicle 610 being a boat. In some embodiments, a boat may arrive at a sea-based material sourcing site, such as an offshore natural gas extraction site, with a store of liquid nitrogen (or other cooling material). The liquid nitrogen may then be used to process the material from site 602-608 on the boat, for instance, to separate constituent parts of the materials sourced from the sea-based sites. For instance, methane and $CO_2$ may be separated and extracted in the hold (e.g., in a tank) of a ship as it returns to shore or continues to another offshore site. Thus, and according to embodiments, a ship may leave its port with liquid nitrogen and return with separated liquid and/or solid methane derived from an offshore installation. In some embodiments, a ship may have enough liquid nitrogen to sequential process materials from multiple offshore sites.

Figure 7:
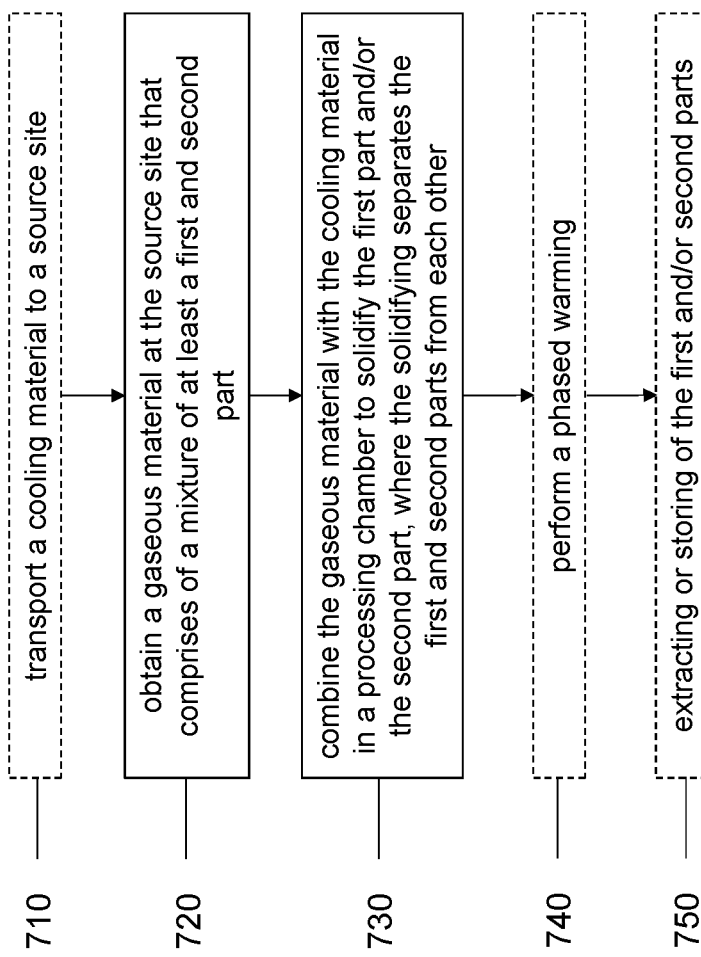
FIG. 7 is a flow chart showing methods according to some embodiments.

Referring now to FIG. 7, a method 700 for mobile processing of materials is provided according to some embodiments. The method may be used, for instance, with system 100 or 200 mounted on a vehicle. The vehicle may be land-based, such as a car, truck, or tractor. Other embodiments may use sea-based or air-based vehicles, such as boats (e.g., tankers) and aircraft. In some embodiments, method 700 may be used for processing materials sourced from remotely located anaerobic digesters, for instance, from one or more farms. In some embodiments, method 700 may be used for processing materials from other gas sources, such as offshore installations, ground wells, or covered gas releases.

The method 700 may begin with step 710, in which a cooling material is transported to a source site. The cooling material may be, in some embodiments, liquid nitrogen. For example, a truck may be loaded with liquid nitrogen in a processing chamber and then drive to a source site, such as a farm. As another example, the hold of a ship may be loaded with liquid nitrogen, and then the ship can then travel to an offshore gas installation. In some embodiments, step 710 may be optional, as the cooling material may be present at the gas source site.

In step 720, a gaseous material is obtained at the source site that comprises a mixture of at least first and second parts. For instance, a gas may be obtained that comprises methane and $CO_2$. This could include, as examples, flowing biogas from an anaerobic digester via a pipe or hose, or natural gas from an offshore installation or covered gas release. In some embodiments, this includes connecting a pipe or hose between the source and processing chamber, and may also include opening a valve of the processing chamber.

In step 730, the gaseous material is combined with the cooling material in a processing chamber to solidify at least one of the first part and the second part, where the solidifying separates the first and second parts from each other. For instance, both the first and second parts may solidify in some embodiments. The separation may occur, for instance, while the mobile plant is in transit. For example, while a ship returns from an offshore installation or while a truck drives from a first farm to a second.

In step 740, which may be optional in some embodiments, a phased warming is performed. The warming may include, for instance, a first phase targeted to methane, and then a second phase targeted to $CO_2$. For instance, a first target temperature may be set for liquid methane, and a second target temperature set for gaseous or liquid $CO_2$. The phased warming may occur, for instance, while the mobile plant is in transit. For example, while a ship returns from an offshore installation or while a truck drives from a first farm to a second.

In step 750, which also may be optional in some embodiments, one or more of the first and second parts are extracted or stored. They may be extracted or stored in solid, liquid, and/or gaseous form. For instance, in conjunction with the phased warming 740, one or more of the constituent parts may be extracted in liquid form. The extraction and/or storage may occur, for instance, while the mobile plant is in transit. For example, while a ship returns from an offshore installation or while a truck drives from a first farm to a second.

Figure 8:
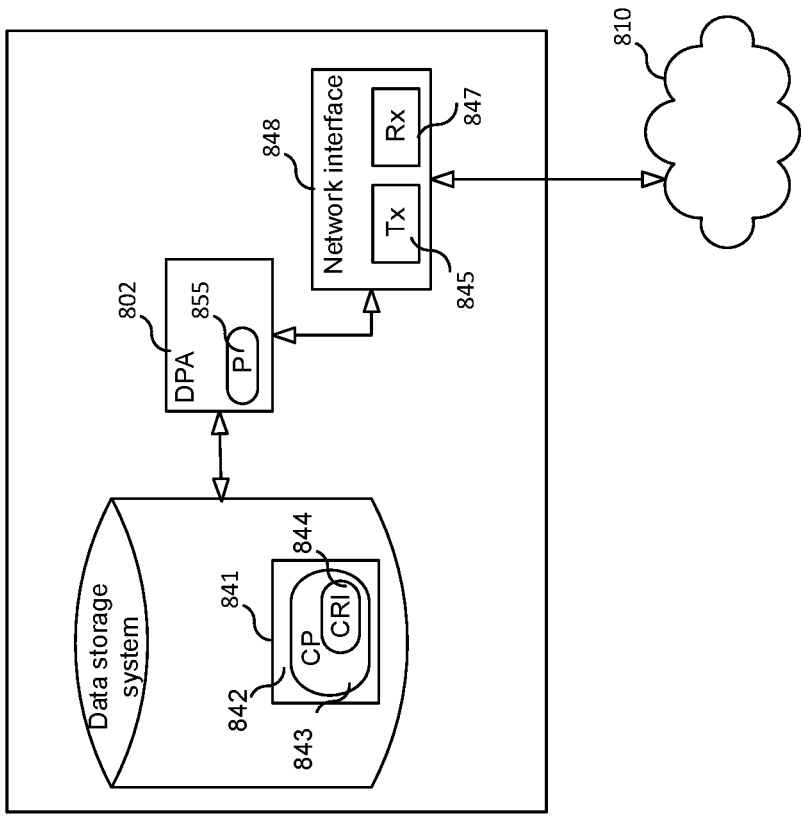
FIG. 8 illustrates a processing and communications device that can be used according to some embodiments.

Referring now to FIG. 8, a block diagram of an apparatus 800 is illustrated. Apparatus 800 may be associated with a processing system 100, 200, mobile processing plant 610, or logistics coordination center 614, according to some embodiments. As shown in FIG. 8, the apparatus may comprise: processing circuitry (PC) 802, which may include one or more processors (P) 855 (e.g., a general purpose microprocessor and/or one or more other processors, such as an application specific integrated circuit (ASIC), field-programmable gate arrays (FPGAs), and the like); a network interface 848 comprising a transmitter (Tx) 845 and a receiver (Rx) 847 for enabling the apparatus to transmit data to and receive data from other nodes connected to a network 810 (e.g., an Internet Protocol (IP) network) to which network interface 848 is connected; and a local storage unit (a.k.a., "data storage system") 808, which may include one or more non-volatile storage devices and/or one or more volatile storage devices. In embodiments where PC 802 includes a programmable processor, a computer program product (CPP) 841 may be provided. CPP 841 includes a computer readable medium (CRM) 842 storing a computer program (CP) 843 comprising computer readable instructions (CRI) 844. CRM 842 may be a non-transitory computer readable medium, such as, magnetic media (e.g., a hard disk), optical media, memory devices (e.g., random access memory, flash memory), and the like. In some embodiments, the CRI 844 of computer program 843 is configured such that when executed by PC 802, the CRI causes the apparatus to perform steps described herein (e.g., steps described herein with reference to the flow charts). In other embodiments, the apparatus may be configured to perform steps described herein without the need for code. That is, for example, PC 802 may consist merely of one or more ASICs. Hence, the features of the embodiments described herein may be implemented in hardware and/or software. According to embodiments, apparatus 800 comprises, or is coupled to, one or more sensors. Such sensors may be used, for instance, to monitor processing in systems 100 and 200 and to control one or more aspects thereof, such as temperature control, material flow, and valve actuation. The sensors may be temperature and/or pressure sensors according to embodiments. In certain aspects, the sensors use sonic transducers to evaluate one or more of volume, flow, and purity.

Figure 9A:
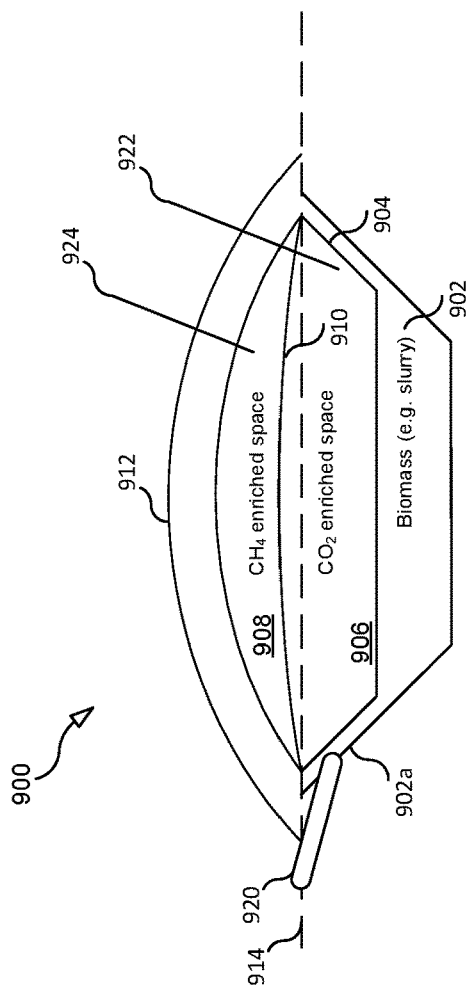
FIGS. 9A and 9B illustrate gas sealing and capture systems according to some embodiments.
Figure 9B:
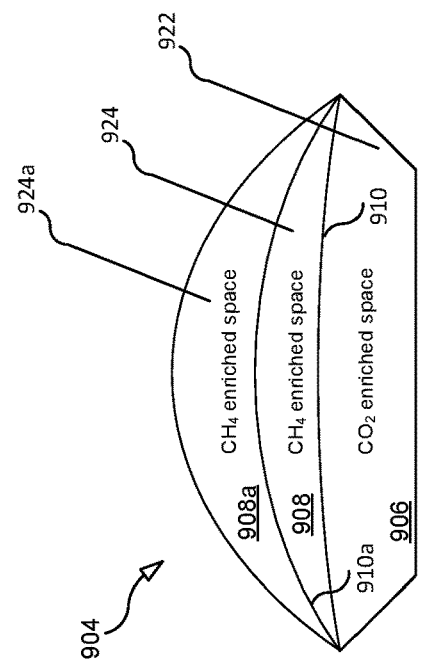

Referring now to FIGS. 9A and 9B, an example of a materials source 900, such as an anaerobic digester, is illustrated according to some embodiments. In some embodiments, the source 900 may take the form of a sealed slurry lagoon. Other sources of gas, such as biogas or natural gas, may also be sealed in order to capture gas for processing according to embodiments. This could include sites that leak natural gas, such as fracking sites, or other ground-based gas sources, including those found in the tundra and landfill sites. Such gas sources can be sealed according to embodiments and used as the gas source for disclosed separation and extraction techniques. For example, they may be sealed in the same manner as illustrated with respect to FIGS. 9A and 9B, which use the non-limiting example of a sealed slurry lagoon.

FIG. 9A illustrates a biogas storage container 904 according to some embodiments. As shown in this example, which uses an anaerobic digester as source 900, the digester includes a biomass storage container 902 for storing biomass (such as slurry) and a biogas storage container 904 for storing biogas resulting from the anaerobic digestion of biomass. The biogas storage container 904 is separated by a semi-permeable membrane 910 into a first space 908 and a second space 906. The membrane may be, for instance, selectively permeable to methane vs. $CO_2$, allowing one to pass and the other not to pass (or pass more slowly). As shown, the second space 906 is $CO_2$ (carbon dioxide) enriched, while the first space 908 is $CH_4$ (methane) enriched. According to embodiments, the material be processed (e.g., in accordance with any of FIGS. 1-8) may be sourced from the first space, the second space, or both. Similarly, the material may be sourced from a sealed gas source having only a single space (e.g., without selective separation before processing).

The anaerobic digester 900 may also include a cover 912, which may be positioned over the biogas storage container 904 in order to protect the biogas storage container 904 from the elements. This could include, for instance, protection from rain and/or wind. Cover 912 may be transparent, and may also provide for passive solar heating of the biogas storage container 904. It should be strong, chemically inert and immune to damage from ultraviolet light. An example may include Ethylene Tera Fluoro Ethylene (ETFE), though other materials may be suitable. The second space 906 of the biogas storage container 904 and the biomass storage container 902 may be coextensive. That is, in some embodiments, there may be no physical separation between the biomass storage container 902 and the second space 906 of the biogas storage container 904.

The anaerobic digester 900 may also include an input 920 for receiving biomass (such as slurry) into the biomass storage container 902. Additionally, anaerobic digester 900 may include output valves 922 and 924, coupled respectively to the second space 906 and first space 908 of the biogas storage container 904. That is, the biogas located within the biogas storage container 904 may be removed from the biogas storage container 904 by pipes or hoses connecting to one or more of output valves 922 and 924. Such pipes and hoses may connect to a mobile or fixed processing plant, and provide enriched biogas to such a processing plant. For instance, they may connected to system 100, 200, and/or 610.

The anaerobic digester 900 may be installed underground, or partially underground. As shown, ground level 914 is indicated in FIG. 9A by a dashed line. In the embodiment shown, the biomass storage container 902 is entirely underground, the second space 906 of the biogas storage container 904 is partially underground and partially above ground, and the first space 908 of the biogas storage container 904 is above ground. Other configurations are possible. Anaerobic digester 900 may be installed by digging a pit in the ground. The pit may include inclined banks 902*a*. In some embodiments, there may be additional layers, such as an insulation layer provided between the ground and the biomass storage container 902. For instance, an insulation layer could prevent the slurry or other biomass from seeping into the ground, or prevent the biogas from escaping the anaerobic digester 100. In some embodiments, one or more of the cover 112 and membranes 910 are used to cover and seal a ground source of gas.

In some embodiments, the digester 900 also provides additional benefits to small- to mid-sized farms in that they can economically employ anaerobic digestion where before it was not feasible. Because such farms may be in remote and diverse geographic locations, it is important that in some embodiments anaerobic digester 900 is a simple design that can be readily implemented at such sites, with readily available equipment and processes. Similar concepts may apply to non-digester implementations, including sealing natural gas sources in locations that are difficult to reach. In some embodiments, rather than using an enclosure above ground (as is standard industrial practice), the digester 900 may be made up of an excavated hole with banks made from the removed earth. This can negate the need for removal of soil from the site and can also negate the need for concrete.

Furthermore, and according to some embodiments, by tapering the walls at an angle, the space above the digester 900 is increased so that it can hold sufficient quantity of biogas to maintain the needs of the periodic biogas processing and collection service in accordance with the space required for biogas generation from the slurry from a defined number of cows. That is, a mobile biogas processing plant may service a remote farm employing anaerobic digester 900, and may make periodic visits, or visits at aperiodic intervals. Accordingly, the digester 900 should have enough space for storing biogas that is expected to be generated before a next arrival time of the mobile biogas processing plant. Tapering the walls at an angle is one way to maximize the available space.

Anaerobic digester 900 may additionally include one or more sensors. For instance, digester 900 may include one or more sensors for measuring an amount of biomass present in the digester 900, an amount of biogas present in the digester 900, an amount of biogas present in each of the spaces (e.g. spaces 906, 908, 908*a*) of the biogas storage container 904, and/or a concentration of biogas present in the digester 900 or in each of the spaces of the biogas storage container 904. Such sensors may also include sensors to measure pressure and other process variables relevant to managing the biogas, such as detection of impurities. According to embodiments, the measurements are made with sensors using one or more sound waves. In certain aspects, the measurements are based on the measured speed of one or more sound waves. For instance, anaerobic digester 900 may include a first transducer coupled to one or more of the digester's gas-containing regions (e.g., 906, 908, 908*a* and/or feed pipes and hoses associated with the digester), where the transducer is configured to generate a first sound wave passing in a first direction through the gas. There may also be a second transducer coupled to the system to receive the first sound wave passing in the first direction through the gas or fluid flowing along the feed pipe. There may also be timing-circuitry in electrical communication with the first and second transducers and configured to measure a velocity of the first sound wave passing in the first direction from the first transducer to the second transducer. This can indicate one or more of amount of biogas, quality of biogas, etc. These same types of sensors and measurements may be used with the processing of the material, for instance, in systems 100 and 200.

In some embodiments, source sites, such as anaerobic digester 900 may also include circuitry and other equipment in order to be able to communicate (e.g. wirelessly communicate) such sensor readings to remote sites, including the logistics coordination center 614 discussed above with reference to FIG. 6. Anaerobic digester 900 may also be able to receive commands and/or configuration settings from a remote site, including the logistics coordination center 614, that cause anaerobic digester 900 to perform some action such as adjusting a setting or configuration of the digester 900.

Biogas produced by anaerobically digesting the slurry can be pre-processed prior to liquefaction. In embodiments, such processing may include cleaning, such as by passing the biogas through a hydrogen sulfide removal system (such as activated charcoal filters). These filters may be located on the mobile biogas processing plant, implemented by one or more membranes of the anaerobic digester 900, or may be fixed installations nearby the anaerobic digester 900. The cleaning can further include drying to remove water vapor (such as by using an industrial dryer). The biogas can be passed from the anaerobic digester to the cleaning components due to the pressure generated in the anaerobic digester 900. According to embodiments, the digester (900) is maintained at positive pressure relative to the outside space as a result of the digestion of biomass in container 902. A low-pressure return valve (located on one or both ends of the connection coupling the anaerobic digester 900 and the filters for processing the biogas) ensures one-way passage through the system. This negates the need for a compressor in the processing/cleaning component, whereas in typical industrial-scale biogas cleaning and upgrading, the use of a compressor is required to force the biogas through the cleaning circuit and also through permeable gas membrane filters which are tightly packaged. A compressor like that used in such systems increases complexity and cost, and also requires additional power, which would lower the overall efficiency of the process. Accordingly, in embodiments anaerobic digester 900 advantageously does not include a compressor. Likewise, the systems 100 and 200 can be implemented without the use of a compressor, and processes 300, 400, 500, and 700 can be performed without a compressor, in some embodiments.

The biogas storage container 904, as described above, is separated into two spaces (906 and 908) by a semi-permeable membrane 910 in FIG. 9A. The semi-permeable membrane 910 may comprise, for example, polytetrafluoroethylene (e.g., expanded PTFE (ePTFE), often referred to as Gore-Tex or Teflon) or silicone. This membrane material is selected to preferentially pass either methane or carbondioxide, for instance, where methane is lighter than carbon dioxide and is also a relatively large molecule compared with carbon dioxide. Other materials may be selected to exploit other variations between methane and carbon dioxide molecules.

As shown in FIG. 9A, the second space 908 is positioned higher than the second space 906. A valve may be positioned to cause biogas from the slurry to move into one of the upper spaces (e.g., by pumping or natural pressurization), such as second space 908. One or more hoses or pipes may also be used. This can be beneficial because gravity can aid in the diffusion or filtering process, helping to make the second space 906 more carbon dioxide enriched and the first space 908 more methane enriched. In some embodiments, there may be additional membranes creating more than two spaces in the biogas storage container 904. For example, there may be a second membrane 910a (see FIG. 9B), and the first and second membrane would then separate the container 904 into three spaces, first space 908, second space 906, and an additional third space 908a that would contain more pure methane than the first space 908. In some embodiments, biogas from the space 902 may be fed to a middle space (e.g., space 908 in FIG. 9B). According to embodiments, a space in the digester 900 can serve as a receiving space.

While two or three spaces are used as an example in some embodiments, there may be more. For instance, there may be more than two membranes (e.g. from three to ten membranes, and even more than that in some embodiments), and thus more than three spaces (e.g., from 4-11). Different membranes may have differing properties to control the relative flow of enriched gas. For instance, differing membranes may be used to filter different materials. For instance a first membrane may selectively filter carbon dioxide, a second membrane may selectively filter water, a third membrane may selectively filter hydrogen sulfide, and a fourth membrane may selective filter water. Thus, and according to embodiments, a digester or sealing member with 1, 2, 3, or 4 membranes is provides. Similarly, and according to embodiments, a digester or sealing member with 2, 3, 4, or 5 spaces is provided. According to some embodiments, one or more pipes, hoses, and valves may be used to direct (e.g., by pumping or natural pressurization) the unfiltered-gas to a selected space to start the filtration process. Such filtering an serve as pre-processing for systems 100 and 200.

In some embodiments, by stacking multiple spaces on top of one another, and through the use of multiple semipermeable membranes, the diffusion process may be improved. For instance, methane may slowly progress upwards through the (vertically stacked) spaces while $CO_2$ moves progressively down, e.g. due to the differences in density and molecule size, and therefore the purity of the methane may increase as a function of both height and time. In such embodiments, there may also be additional valves (such as valve 924a) for removing the methane from the additional spaces, as it can be more efficient to process methane that is more pure. Also, it may be beneficial to have a relatively leaky membrane closer to the bottom and less leaky closer to the top to allow more of the heavier larger CO2 molecules to drop down. The permeability of the various semi-permeable membranes may differ (e.g. they may have different pore sizes), and for example, could be optimized for gas production or methane purity. In some embodiments, a membrane used to selectively filter a material from methane may have a separation factor of between 3.0 and 40 depending on material (e.g., 3.42 for CO2, 10.5 for hydrogen sulfide, and 37.9 for water). Similarly, there may be relative separation factors between the filtered materials (e.g., 3.6 between water and hydrogen sulfide and 11.7 between water and CO2). Such selective permeability can be used advantageously in a stacked arrangement for a digester 900. A gas may become more refined when passing through different spaces and membranes.

In some embodiments, a composite membrane may be used, in which two or more membranes are combined. This can be used, for example, to add additional filtering properties (e.g., where the second membrane also selectively filters) or for improved strength and control of the membrane. For instance, a filtering membrane may be layered onto a backing material to add rigidity or support. According to an embodiment, the physical strength required to be self-supporting over a large area may be improved with a composite membrane, where the strength and porosity of a particular material (e.g., a aramid or para-aramid material such as Kevlar or PTFE-based material such as Gore-tex) is used as a backing material to a highly-selective silicone membrane to control the stretching of the silicone pores, which might change the properties of the membrane. Feed and permeate pressures can affect permeation rates as the membrane structure can change under pressure. For example, if the membrane is stretched, then the pore size may change leading to a change in the separation factor. According to embodiments, the membrane may be asymmetrical, such that the filtering properties are different depending on the direction of gas flow. This may be based, for instance, on the permeation behaviour seen in $CO_2/CH_4$ mixtures in the cellulose acetate membrane system, for example.

Typical filtration requires use of a compressor with outputs typically in the range 5-15 bar pressure. However, according to embodiments, the biogas storage volume provides sufficient space for a large surface area of selectively permeable membrane, such as 500-10,000 $m^2$. Such a configuration offers a very low flow resistance through which the biogas constituents are enriched. Coupled with the fact that, in some instances, time is not necessarily a driving factor, molecular mass and molecule size provide a natural selective permeation process across the membrane. The enrichment process may still be enhanced through a pressure differential, but at a significantly lower levels, for instance in the 10-300 mB range.

The stretching of the membrane under moderate pressure could be used advantageously where changing or controlling the pressure in any one of the storage volumes is used to tune the separation factor between the gas constituents, and thereby used to speed up or slow down the separation process for optimization. For example, the separation factor of a particular membrane may be different from batch to batch due to variations in manufacturing process variables between manufacturers. By adjusting the relative pressure in each volume the membrane can be stretched or allowed to relax increasing or decreasing pore size respectively. As the separation factor may be strongly reliant of the average pore size, it can be adjusted accordingly. This could also solve issues of clogging due to moisture vapour, particulates etc. According to embodiments, if clogging becomes an issue, the pressure could be increased stretching the membrane and its pores to a point where the clogging is alleviated and the H2O and particulates pass through the membrane. This step could be introduced into a biogas refining operating procedure to extend the life of the membrane, including as a step in any of the anaerobic digester operations described herein.

In certain aspects, a method of operating an anaerobic digester can include a step of self-cleaning through membrane stretching, e.g., by pressurized flow through one or more membranes.

According to embodiments, a batch process is provided with continual refinement by moving gases through successive passes through the system. In certain aspects, the gas may move through continuously. In certain aspects, the gas is at low pressure (e.g., using a blower). In certain aspects, a compressor is not used.

Depending on the purity required for a particular purpose, the gas can be taken out at the appropriate space within the stack. The process of ultra-low pressure diffusion-enhanced molecular refinement is slow, taking place over days. This is accounted for by keeping the volume of the biogas storage container 904 sufficiently large so as to be able to hold the biogas generation capacity of the anaerobic digester at least over a similar period.

In some embodiments, biogas that is at a higher level in the biogas storage container 904 may be passed down to a lower level or vice versa. For instance, biogas in space 908 and/or space 908a may be fed back to space 906. The gas may be fed back by using a low-pressure pump (which may be solar powered). Doing this causes the biogas to go through a gravitation-assisted diffusion process another time. Such additional refinement can improve the separation of methane and carbon dioxide. Because the biogas may be stored in the biogas storage container 904 for an extended period of time (e.g., days and/or weeks) before being retrieved and processed by a mobile processing plant, there is ample time to allow for additional refinement by pumping the gas at a higher level to a lower level of the biogas storage container 104 or vice versa.

Typical ratios of methane to $CO_2$ in raw biogas are about 60:40 or 70:30. In embodiments, after an extended period (e.g. to allow for the ultra-low pressure diffusion-enhanced refinement due to the semi-permeable membrane 910), this ratio will rise to 85:15 in the upper space (i.e. first space 908) and reduce to ~35:65 methane to carbon dioxide in the lower space (i.e. second space 906). The membrane material may be optimized to increase the first ratio (that is, the methane-to-carbon-dioxide ratio in the second space 906) and reduce the second ratio (that is, the methane-to-carbon-dioxide ratio in the first space 908) over the likely primary refinement and collection period. For subsequent processing by the mobile processing plant, it is advantageous to have the first space 908 be $CH_4$ enriched (e.g. greater than 60:40 ratio, such as an 85:15 ratio or higher) and the second space 906 be $CH_4$ depleted (e.g. less than 60:40 ratio, such as a 35:65 ratio or lower). However, systems 100 and 200 can be used without pre-enrichment of the source material in embodiments, and can be operated with methane of varied purities.

In certain aspects, the anaerobic digester 900 operates more efficiently compared to other systems. For instance, a degree of heating is provided by the greenhouse effect enabled by the use of a clear, transparent cover 912 (such as a plastic roof). The cover 912 also stops rainwater from cooling the upper surface of the biogas storage container 904. The digester's size can be varied to allow for different anaerobic digestion timescales. For instance, the digester can be made sufficiently large to allow for a very slow, long anaerobic digestion process. This can result in a more efficient conversion of biomass material to biogas. For example, a retention period of 200 days can be accommodated. Such a period aligns with the annual digestate management period for a typical dairy farm, whereas the standard industrial scale anaerobic digester would have a retention period of about 40 days. The digester design also removes the requirement for stirring systems, which can be complicated, unreliable, and power hungry. According to some embodiments, one or more of the permeable membranes is removable, such that they can be periodically cleaned or replaced.

Additionally, much of the gas refinement is carried out slowly, at low pressure, enhanced by diffusion through the use of a simple semi-permeable membrane before final refinement using a fast, high-pressure system. This two-stage refinement improves the overall energy efficiency of the gas refinement process. Additionally, in embodiments, there is no investment required by the owner of the anaerobic digester for biogas processing and liquefaction equipment. Similar, covers/membranes can be used to capture gas at locations where the owner will not be investing. Because the digester can be used with a mobile processing plant, the costs required for such processing can be spread to a purchaser of the excess biogas, thereby enabling small- to mid-sized farms the ability to economically utilize anaerobic digestion. Further, because the anaerobic digester provides other benefits in addition to any revenue that may result from sale of excess biogas, a farm owner looking to install this equipment need not focus solely on the gas production rate to determine the value of investment in this equipment. Any revenue from gas sales would be a bonus on top of the other available benefits. Also, the investment case for the biogas processing plant is also different. The costs of the biogas processing plant, because it is mobile, may be spread out among the purchasers of biogas or the multiple farms that may utilize a single mobile biogas processing plant. Additionally, because the plant is mobile, it can effectively be in use continuously (apart from travel time), which also improves the investment case for such a plant.

According to embodiments, aspects of a mobile processing plant (e.g., for processing gas having at least two constituent parts) such as plant 610 are now described, the plant comprises not only separation equipment, such as system 100 or 200, but also refrigeration, liquefaction, and/or storage elements. In embodiments, an ultra-compact, efficient, and self-powering mobile biogas separation and liquefaction processing plant is provided. In some embodiments, liquefaction may take place in a separation chamber 102, 202 of system 100, 200. This may use, for instance, one or more refrigeration elements to process methane that has returned to a gaseous state in the chamber. For example, a gas may be processed to obtain separated methane with the $CO_2$ removed, and then sealed in a container (e.g., in the chamber 102, 202). As the container warms, methane may return to a gaseous state and then re-liquefied using equipment of the plant 610. In embodiments, a separate element, such as a tank, may be coupled to system 100, 200 to perform liquefaction of methane that had been previously processed in chamber 102, 202 of system 100, 200. The separate liquefaction element may also be mounted on the mobile plant 610. In embodiments, liquefaction techniques as described in U.S. Pat. No. 9,927,067, which are incorporated herein by reference, are implemented in either the processing chamber 102, 202 or separate element (e.g., liquefaction chamber or tank).

While various embodiments of the present disclosure are described herein, it should be understood that they have been presented by way of example only, and not limitation. Thus, the breadth and scope of the present disclosure should not be limited by any of the above-described exemplary embodiments. Moreover, any combination of the above-described elements in all possible variations thereof is encompassed by the disclosure unless otherwise indicated herein or otherwise clearly contradicted by context.

Additionally, while the processes described above and illustrated in the drawings are shown as a sequence of steps, this was done solely for the sake of illustration. Accordingly, it is contemplated that some steps may be added, some steps may be omitted, the order of the steps may be re-arranged, and some steps may be performed in parallel.

The invention claimed is:

1. A method of processing, comprising the steps of:
   obtaining a source material, wherein the source material is comprised of a mixture of at least a first part and a second part;
   combining the source material with liquid nitrogen in a processing chamber to solidify one or more of the first part and the second part, wherein the solidifying separates the first and second parts from each other; and
   performing a phased warming of at least one of the processing chamber, solid first part, and solid second part.

2. The method of claim 1, further comprising:
   sealing the processing chamber to store one or more of the first and second parts.

3. The method of claim 1, wherein the first part is methane and the second part is carbon dioxide.

4. The method of claim 1, wherein the source material is a biogas and obtaining the source material comprises receiving the biogas from an anaerobic digester via hose or pipe, further comprising:
   generating the biogas in the anaerobic digester.

5. The method of claim 1, further comprising:
   circulating liquid nitrogen through the processing chamber to maintain a desired temperature in the processing chamber or a liquid nitrogen reservoir.

6. The method of claim 1, further comprising:
   cooling one or more of a liquid nitrogen source or a gas input using vented nitrogen from the processing chamber, or
   liquefying vented nitrogen and providing the liquefied nitrogen to the processing chamber.

7. The method of claim 3, wherein the processing chamber has a first region and a second region, and wherein the combining is performed in the first region, further comprising:
   collecting solid methane in the second region.

8. The method of claim 7, wherein the first and second region are separated by a vertical divider that allows solid methane to flow over the divider in a single direction based on a flow of liquid nitrogen.

9. The method of claim 1, wherein the phased warming comprises:
   warming at least the first part to a first temperature in a first warming phase; and
   extracting the first part from the processing chamber in liquid form.

10. The method of claim 9, wherein the phased warming comprises:
    warming at least the second part to a second temperature in a second warming phase; and
    extracting the second part from the processing chamber in gaseous or liquid form.

11. The method of claim 10, wherein the first part is methane and the first temperature is at least 90 degK, and wherein the second part is carbon dioxide and the second temperature is at least 194 degK.

12. The method of claim 1, wherein the phased warming comprises the activation and deactivation of a heating element, or the phased warming comprises the activation and deactivation of a refrigeration device.

13. The method of claim 1, further comprising:
    covering a gas producing source with one or more of a cover and membrane, and wherein the obtaining of the source material is from the covered source.

14. The method of claim 1, wherein both the first part solidifies and the second part solidifies as a result of the combining.

15. The method of claim 1, wherein the processing chamber is a cryogenic storage tank under vacuum.

16. The method of claim 1, wherein the processing chamber is mounted on a mobile processing plant and separating of the first and second parts is performed while the mobile plant is in transit away from a source site.

17. The method of claim 1, wherein the processing chamber is mounted on a mobile processing plant and the phased warming is performed while the mobile plant is in transit away from a source site.

18. A method of processing, comprising the steps of:
    obtaining a source material, wherein the source material is comprised of a mixture of at least a first part and a second part; and
    combining the source material with liquid nitrogen in a processing chamber to solidify one or more of the first part and the second part, wherein the solidifying separates the first and second parts from each other,
    wherein the processing chamber is an uncovered chamber.

* * * * *